United States Patent [19]
Borst et al.

[11] Patent Number: 6,110,428
[45] Date of Patent: Aug. 29, 2000

[54] DEVICE FOR USE IN THE ISOLATION OF A BIOLOGICAL MATERIAL SUCH AS NUCLEIC ACID

[75] Inventors: Govert Arnoldus Petrus Borst, Vught; Johannes Antonius Gerardus Wilhelmus Zigmans, Rotterdam, both of Netherlands; Benjamin Joseph Chemelli, Durham, N.C.; Donald Robinson, Lakeland, Fla.

[73] Assignee: Akzo Nobel N.V., Arnhem, Netherlands

[21] Appl. No.: 08/793,482

[22] PCT Filed: Aug. 28, 1995

[86] PCT No.: PCT/EP95/03385

§ 371 Date: May 27, 1997

§ 102(e) Date: May 27, 1997

[87] PCT Pub. No.: WO96/06850

PCT Pub. Date: Mar. 7, 1996

[30] Foreign Application Priority Data

Aug. 29, 1994 [NL]  Netherlands .......................... 9401391

[51] Int. Cl.[7] ............................ B01D 29/90; B01D 29/00
[52] U.S. Cl. ............................ 422/101; 422/58; 422/100; 436/180
[58] Field of Search .............................. 422/58, 100, 101, 422/102, 103, 104; 436/538, 540, 177, 178, 180

[56] References Cited

U.S. PATENT DOCUMENTS

| | | | |
|---|---|---|---|
| 3,647,390 | 3/1972 | Kubodera et al. | 23/252 R |
| 4,483,920 | 11/1984 | Gillespie et al. | 435/6 |
| 4,746,490 | 5/1988 | Saneii | 422/62 |
| 4,800,159 | 1/1989 | Mullis et al. | 435/172.3 |
| 4,956,298 | 9/1990 | Diekmann | 430/311 |
| 4,995,967 | 2/1991 | Van Driessche | 210/94 |
| 5,039,488 | 8/1991 | Kohr | 436/181 |
| 5,053,454 | 10/1991 | Judd | 525/54.11 |
| 5,073,341 | 12/1991 | Hargreaves | 422/58 |
| 5,114,858 | 5/1992 | Williams et al. | 435/270 |

(List continued on next page.)

FOREIGN PATENT DOCUMENTS

| | | |
|---|---|---|
| 0 487 028 A2 | 5/1992 | European Pat. Off. . |
| WO95/02049 | 1/1995 | WIPO . |
| WO97/32645 | 9/1997 | WIPO . |

OTHER PUBLICATIONS

Belgrader et al. *Biotechniques* 19 (1995) No. 3, 426–428.
Peyman et al. *BioTechniques* 16 (1994) No. 2, 210.
Lear et al. *Am Biotechnol. Lab.* 13 (1995) No. 3, 100.
Derwent Abstract No. 95–382762 (1994).
Derwent Abstract No. 94–293557 (1985).
Derwent Abstract No. 95–044223 (1993).
Derwent Abstract No. 95–090549 (1993).
Derwent Abstract No. 95–200378 (1993).
Derwent Abstract No. 95–206804 (1993).
Derwent Abstract No. 95–240775 (1993).

(List continued on next page.)

*Primary Examiner*—Jill Warden
*Attorney, Agent, or Firm*—Gregory R. Muir

[57] ABSTRACT

A device is used for the isolation of a biological material from a basic material containing the biological material. The device includes a container for holding a mixture of the basic material, a chaotropic substance and a solid phase which binds the biological material. The device also includes a filter for separating the solid phase with the biological material from the fluid bound thereto, and a connector for connecting and disconnecting the container to an inlet for washing fluid and eluant fluid, as well as a connector for connecting and disconnecting the container to an outlet for the washing fluid after washing the biological material bound to the solid phase, as well as a connector for connecting and disconnecting the container to an eluate reservoir for collection of the eluant fluid with the dissolved biological material.

14 Claims, 3 Drawing Sheets

U.S. PATENT DOCUMENTS

| | | | |
|---|---|---|---|
| 5,139,637 | 8/1992 | MacConnell | 204/299 R |
| 5,208,160 | 5/1993 | Kikyotani et al. | 435/270 |
| 5,234,809 | 8/1993 | Boom et al. | 435/91 |
| 5,284,940 | 2/1994 | Lin et al. | 536/25.4 |
| 5,316,731 | 5/1994 | Schrenk et al. | 422/101 |
| 5,330,914 | 7/1994 | Uhlen et al. | 435/270 |
| 5,330,916 | 7/1994 | Williams et al. | 435/311 |
| 5,346,999 | 9/1994 | Cathcart et al. | 536/25.41 |
| 5,352,609 | 10/1994 | Boquet | 435/270 |
| 5,358,691 | 10/1994 | Clark et al. | 422/64 |
| 5,417,924 | 5/1995 | Di-Martino et al. | 422/101 |
| 5,443,743 | 8/1995 | Fetner et al. | 210/656 |
| 5,451,528 | 9/1995 | Raymoure et al. | 435/533 |
| 5,552,325 | 9/1996 | Nochumson et al. | 436/177 |
| 5,578,459 | 11/1996 | Gordon et al. | 135/29 |
| 5,578,495 | 11/1996 | Wilks | 436/178 |
| 5,593,290 | 1/1997 | Greisch et al. | 417/478 |
| 5,599,504 | 2/1997 | Hosoi et al. | 422/82.08 |
| 5,603,845 | 2/1997 | Holm | 210/782 |
| 5,645,723 | 7/1997 | Fujishiro et al. | 210/321.75 |
| 5,693,785 | 12/1997 | Woodard et al. | 536/25.4 |
| 5,746,978 | 5/1998 | Bienhaus et al. | |

OTHER PUBLICATIONS

Derwent Abstract No. 95–241774 (1993).
Derwent Abstract No. 95–274924 (1992).
Derwent Abstract No. 95–370471 (1994).
Derwent Abstract No. 96–133418 (1994).
Derwent Abstract No. 96–160299 (1994).
Derwent Abstract No. 96–179893 (1994).
Derwent Abstract No. 95–190163 (1993).
Derwent Abstract No. 96–031612 (1994).
Derwent Abstract No. 95–255056 (1994).
Derwent Abstract No. 95–366254 (1994).
Derwent Abstract No. 95–366265 (1994).
Derwent Abstract No. 94–294348 (1993).
Derwent Abstract No. 95–051801 (1993).
Derwent Abstract No. 95–283025 (1993).
Derwent Abstract No. 96–031615 (1994).
Derwent Abstract No. 95–016567 (1993).
Derwent Abstract No. 94–237590 (1992).
Derwent Abstract No. 95–058795 (1991).
Derwent Abstract No. 95–188000 (1993).
Derwent Abstract No. 95–234336 (1993).
Derwent Abstract No. 96–106044 (1994).
Derwent Abstract No. 96–188389 (1994).
Derwent Abstract No. 95–148670 (1993).
Derwent Abstract No. 95–148671 (1993).
Derwent Abstract No. 95–329874 (1994).
Derwent Abstract No. 96–078605 (1994).
Derwent Abstract No. 96–187701 (1989).

6,110,428

DEVICE FOR USE IN THE ISOLATION OF A BIOLOGICAL MATERIAL SUCH AS NUCLEIC ACID

This application is a 371 of PCT/EP95/0385, filed on Aug. 28, 1995.

BACKGROUND OF THE INVENTION

The present invention relates to the isolation of a biological material, for example nucleic acid, from a basic material containing said biological material.

An example of a method for the isolation of nucleic acid is known from U.S. Pat. No. 5,234,809. In the case of this method the basic material, a chaotropic fluid and silica particles are mixed, with the result that the nucleic acid is adsorbed on the silica particles. The silica particles are then separated from the fluid and treated with a buffered eluant, in which the nucleic acid is dissolved off the particles. With this method HIV tests, for example, can be prepared by isolating the nucleic acid from the basic material, which is blood.

The object of the present invention then is to provide a device which is suitable for carrying out the methods described and similar methods.

SUMMARY OF THE INVENTION

To this end, the device according to the invention is characterized by a container for holding a mixture of the basic material, a chaotropic fluid and a solid phase which binds the biological material; means for separating the solid phase with the biological material from the fluid bound thereto; and means for connecting the container to an inlet and outlet for washing fluid for washing the biological material bound to the solid phase, to an inlet for an eluant fluid, and to an eluate reservoir for collection of the eluant with the dissolved biological material.

If the solid phase which binds; the biological material consists of particle material, then it is advantageous if the means for separating the solid phase from the fluid are provided with a filter for allowing through the fluid and retaining the particle material.

The means for connecting the container to the inlet or outlet for eluant fluid and washing fluid and/or to the eluate reservoir are preferably provided with a shut-off element, which can be provided with, for example, a septum and an outlet channel for allowing through fluid from the separating means to the outlet, and also a hollow needle element connecting to the separating means, for piercing the septum in order to connect the separating means to the eluate reservoir.

Such a shut-off element is simple, user-friendly and reliable in operation.

In a preferred embodiment of the device according to the invention the container is provided with two sections lying one above the other and separated by a constriction, and is also provided with a supply element which can be connected to the inlet and is movable between a position above the constriction and a position connecting in a close fit to the constriction.

In this embodiment both compressed gas for discharging the sample fluid from the container and the washing fluid and the eluant fluid can be fed into the container by one and the same supply element. During the infeed of gas the supply element will be in the position above the constriction, following which the supply element is moved to the position connecting suitably to the constriction, so that only the bottom part of the container, containing the solid phase with the biological material bound thereto, need be flushed, with the result that less washing fluid is needed and there is less of a risk of contamination occurring.

In an alternative embodiment the shut-off element is a valve element designed with at least one non-return valve between inlet and container.

In a more advanced development thereof the valve element is provided with three non-return valves: the first-mentioned non-return valve in the connection to a compressed gas supply, a second non-return valve between the container and the separating means, and a third non-return valve in a connection between the separating means and the inlet for the washing fluid and the eluant.

Compared with the embodiment with one valve, this embodiment has the advantage that the washing fluid is introduced directly into the separating means, and the container therefore does not need to be washed, with the result that only a small amount of washing fluid is needed.

BRIEF DESCRIPTION OF THE DRAWINGS

The invention will be explained below with reference to the drawings, which show a number of exemplary embodiments of the device according to the invention.

FIG. 7 is a vertical longitudinal section of a second embodiment of the device according to the invention.

DETAILED DESCRIPTION OF THE PREFERRED EMBODIMENTS

The drawings show exemplary embodiments of a disposable device for use in the isolation of a biological material, such as nucleic acid, from a basic material containing said biological material. The basic material can be, for example, blood, blood serum, urine, faeces, cell cultures and the like. The isolation of the biological material, in particular nucleic acid, is necessary for carrying out tests, such as, for example, an HIV test.

Figure 1:
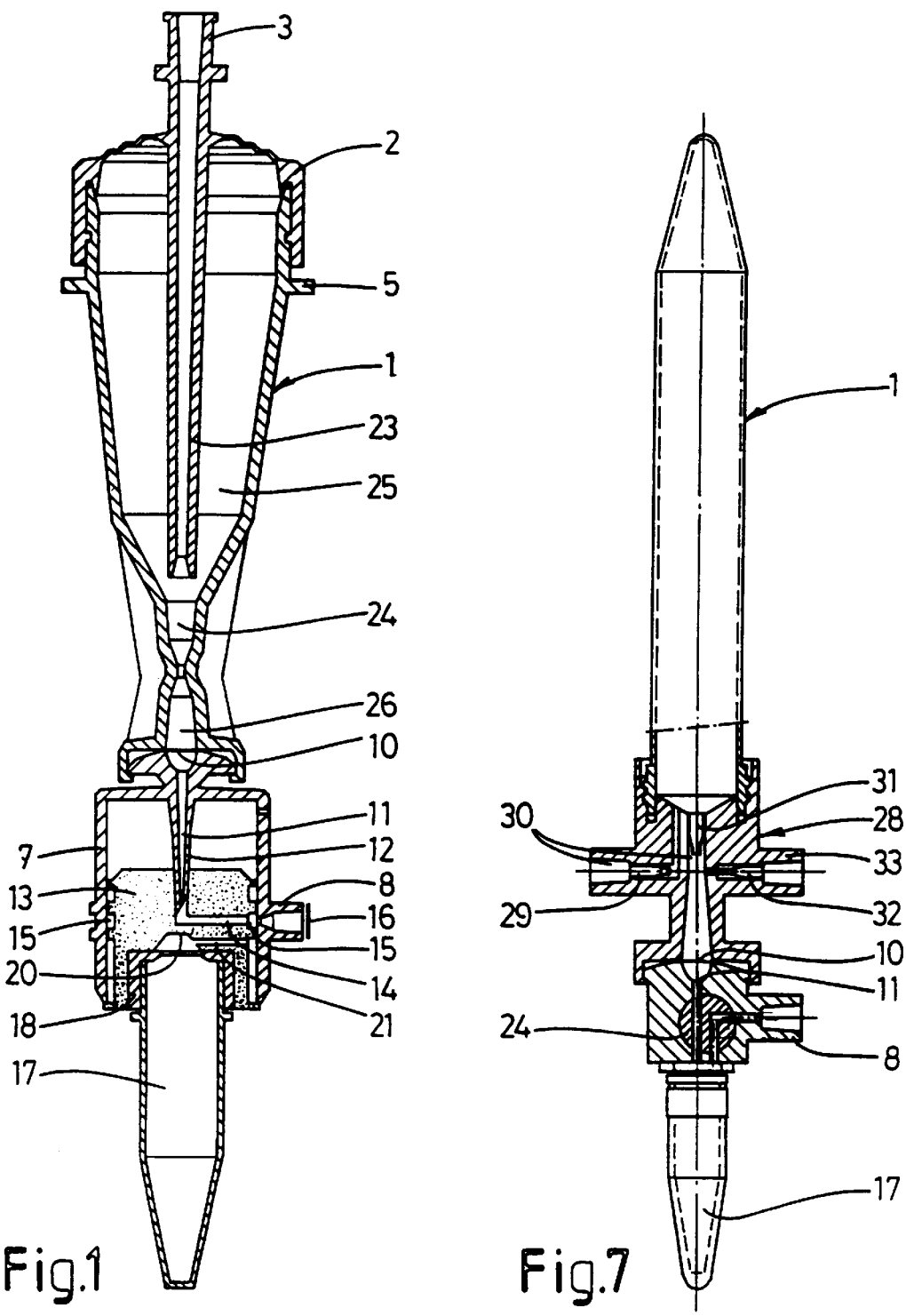
FIG. 1 is a vertical longitudinal section of a first embodiment of the device according to the invention.
Figure 2:
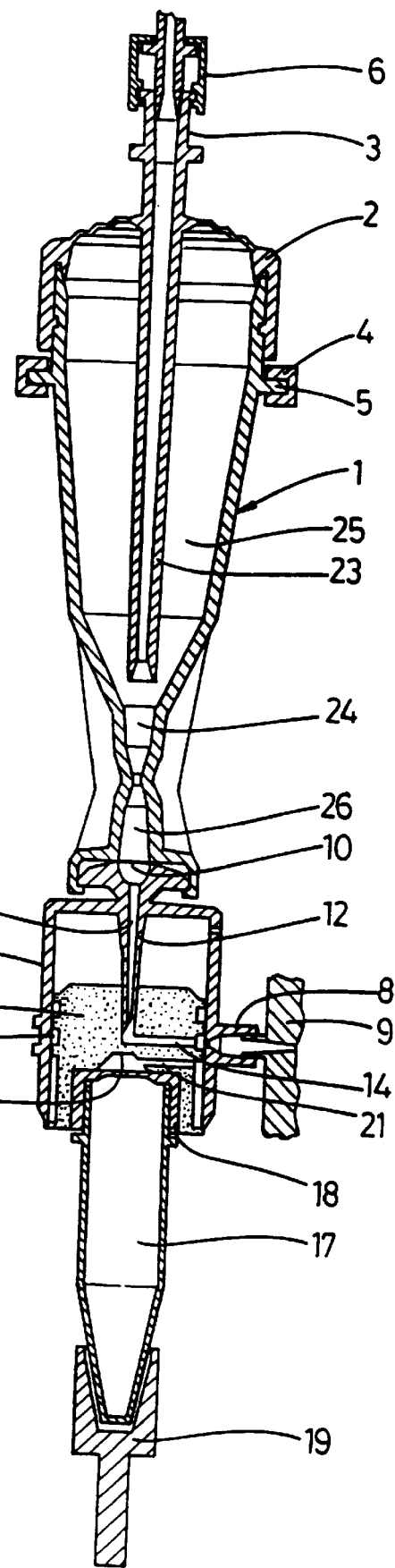
FIG. 2 is a section corresponding to FIG. 1, in which the device according to the invention is placed in a control apparatus.

The device shown in FIGS. 1 and 2 comprises a container 1 for holding a mixture of the basic material, a chaotropic substance and a solid phase which binds the nucleic acid, in this exemplary embodiment silica particles. What is meant by chaotropic substance is any substance which is capable of altering the secondary, tertiary and/or quaternary structure of proteins and nucleic acid, but leaves at least the primary structure intact. Examples thereof are guanidine, (iso) thiocyanate and guanidine hydrochloride. In this exemplary embodiment the container 1 belongs specifically to the device and the sample to be examined must be placed in the container by pipetting. The container is then sealed with a cover 2. The cover 2 is designed with an inlet connection 3, for connection of the container 1 to an inlet (not shown) for compressed air, washing fluid and eluant fluid. These inlets for fluids form part of a control apparatus, parts of which are shown in FIG. 2 and in which the device according to the invention can be placed for carrying out the isolation of the nucleic acid. FIG. 2 shows, for example, a connecting ring 4 for suspending the device in the apparatus, for which purpose the container 1 is designed with a circular flange 5. FIG. 2 also shows a connecting element 6 for the inlets for the fluids, which connecting element can be connected to the inlet connection 3 of the cover 2.

The container 1 forms the top element of the device, which is connected at the bottom end to a bottom element 7. This cylindrical bottom element 7 comprises on the periphery an outlet connection 8 for connecting the device to an outlet for sample fluid and washing fluid, which forms part of the apparatus and is indicated by 9. Clamped between the top end of the bottom element 7 and the container 1 is a membrane 10, which serves as a filter and on which the silica particles with nucleic acid adsorbed thereon can settle. A channel 11 connects to the space below the membrane 10. The channel 11, which forms the passage for a needle 12, comes out in a shut-off element 13, which in this case is provided with a septum 20. The shut-off element 13, of silicone material, is provided with an outlet channel 14 with a top part lying in line with the channel 11 and a bottom part running towards the periphery. At the periphery of the shut-off element 13 the outlet channel 14 opens out into an annular peripheral channel 15 which can be placed in communication with the outlet connection El in the bottom element 7. In the position of the shut-off element 13 shown in FIG. 2 sample fluid and washing fluid can be conveyed out of the container 1, by way of the membrane 10 and the channels 11 and 14 to the outlet 9. A removable sealing plate 16 ensures that the outlet connection 8 is sealed before the device is used. The shut-off element could also be placed initially in a closed position and pushed to a discharge position only when the sample fluid is to be discharged.

The device according to the invention also comprises an eluate reservoir 17 for the collection of an eluant supplied from the inlet connection 3, and containing the nucleic acid dissolved off the silica particles. The eluate reservoir can be a standard cup with a capacity of, for example, 0.5 ml, which is shut off by a septum 18 of silicone material. The eluate reservoir 17 can be placed in a positioning element 19 of the apparatus, and with tnis positioning element 19 eluate reservoir 17 and shut-off element 13 can be pushed up relative to the bottom element 7 with the needle 12, in such a way that the needle cuts open in a sealed-off manner the septum 20 in line with the top part of the outlet channel 14 in the shut-off element 13 and the septum 18 of the eluate reservoir 17, following which eluate supplied can pass into the eluate reservoir 17 without the risk of leakages. A vent channel 21 together with a vent groove in the periphery of the needle 12 (see FIG. 6) ensure that air can escape from the eluate reservoir 17 for the admission of the eluant fluid. The vent channel 21 in the shut-off element 13 can also be combined with the discharge channel 14, while a second needle can also be disposed in the shut-off element for the venting.

Figure 3:
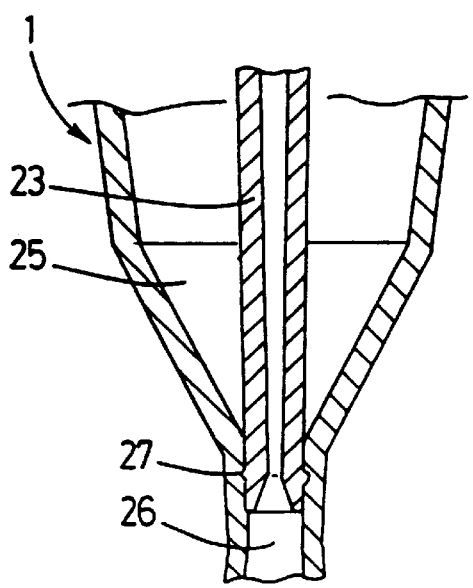
FIG. 3 shows on a larger scale the detail III from FIG. 2, with the supply element in the bottom position.

It can also be seen in FIGS. 1, 2 and 3 that a hollow pin-shaped inlet element 23 is formed in line with the inlet connection 3 of the cover 2, which inlet elements projects until it is deep inside the container 1 and is movable in the container 1 through the special construction of the cover with flexible ridges 24. The container 1 is formed in two parts, namely a top part 25 of large volume tapering downwards towards a constriction 24, and a bottom part 26 of small volume and flaring out slightly downwards from the constriction 24, and connecting to the membrane 10. The inlet element 23 can be moved by means of the connecting element 6 of the apparatus between a top position shown in FIGS. 1 and 2, in which the inlet element 23 opens out above the constriction 24 in the top part 25 of the container 1, and a bottom position, in which the feed element engages in a shut-off manner in the constriction 24 and therefore opens out in the bottom part 26 of the container 1. The inlet element 23 and/or the constriction 24 could be provided with snap means 27 for reliably maintaining the grip.

The device according to FIGS. 1–3 works as follows:

First of all, the mixture of the basic material, the chaotropic substance and the silica particles is placed in the container 1, and the sealed device is then placed in the apparatus in the position shown in FIG. 2. Air is then pumped through the inlet connection 3 and the inlet element 23 into the container 1, in order to build up pressure in the container 1 for promoting the discharge of the sample fluid from it. After this discharge of the sample fluid, only the silica particles with adsorbed material remain behind on the membrane 10, together with residues of the sample fluid. The inlet element 23 is then moved to the bottom position in engagement with the constriction 24, following which a washing buffer (mixture of salts), ethanol and acetone are fed in through the inlet element, in order to wash the silica particles and the cavities and passages of the device in question. Air can also be pumped through intermittently, in order to achieve an additional scraping effect. Finally, conditioned warm air is passed through. The next step is then to move up the positioning element 19, in order to move the eluate reservoir 17 and the shut-off element 13, so that the septums 18 and 20 can be pierced by the needle 12, as a result of which the container 1 enters into communication with the eluate reservoir 17 by way of the filter channel 11. Finally, the eluant fluid, for example in the form of TE buffer, double distilled water or PCR buffer, is fed in through the inlet element 23. The eluant fluid is kept in contact with the silica particles for a predetermined period, following which the eluant fluid is pumped further and passes by way of the membrane 10 and the channel 11 in a predetermined quantity, for example 100 $\mu$l, into the eluate reservoir 17. In this eluant fluid the nucleic acid is dissolved off the silica particles and is ready for testing. The shut-off element 13 and the eluate reservoir 17 are then moved down again, with the result that the needle 12 returns to the discharge position. Remaining eluant fluid is then pumped away to the outlet. When the needle 12 is withdrawn the septum 18 closes automatically, so that a sealed reservoir 17 with the fluid to be examined is obtained.

Figure 4:
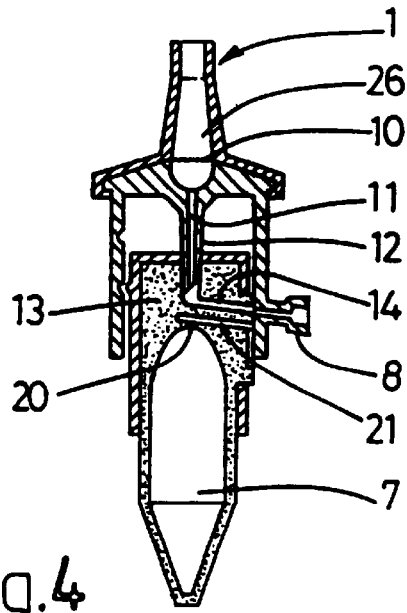
FIG. 4 is a vertical section of an alternative embodiment of a part of the device according to FIG. 1, in which the shut-off element is in the washing position.
Figure 5:
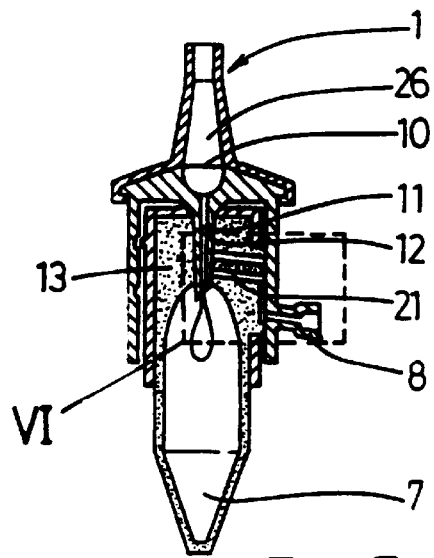
FIG. 5 is a section corresponding to FIG. 4, with the shut-off element in the elution position.
Figure 6:
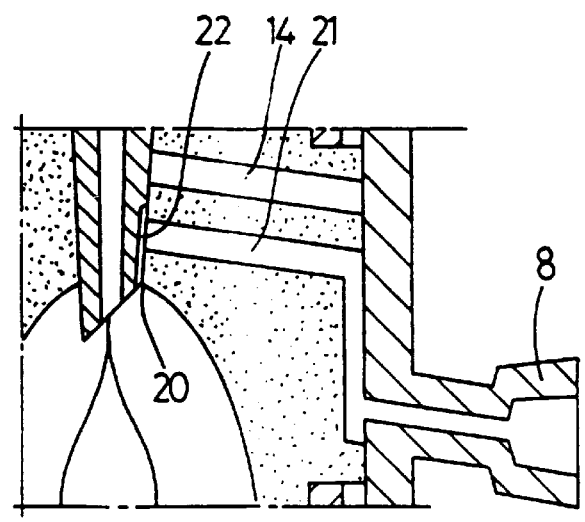
FIG. 6 shows on a larger scale the detail VI from FIG. 5.

FIGS. 4–6 show a variant of the shut-off element 13 and the eluate reservoir 17, which in this case are combined to a fixed unit and together can be moved between the washing or discharge position shown in FIG. 4 and the elution position shown in FIG. 5, moved upwards relative to the position shown in FIG. 4, in which elution position the needle 12 has; pierced through the septum 20 between the outlet channel 14 and the eluate reservoir 17. FIG. 6 shows the abovementioned vent groove 22 in the needle, which ensures that air can escape from the eluate reservoir 17 when the eluant fluid flows into the reservoir. For the rest, the device can be comparable to that of FIGS. 1–3.

FIG. 7 shows an exemplary embodiment of the device according to the invention which is different in principle. In this case the shut-off element is a valve element 28 on which a standard sample rube can be fitted as container 1. The valve element 28 in this exemplary embodiment contains three commercially available non-return valves: a non-return valve 29 in a connecting channel 30 between a compressed gas inlet (not shown) and the container 1, a second non-return valve 31 between the container 1 and filter membrane 10 and channel 11 acting as separating means, and a third non-return valve 32 in a connecting channel 33 between the filter membrane 10 and the channel 11 and the inlet for the washing fluid and the eluant fluid (not shown).

Instead of a pierceable septum in the shut-off element, the valve element 28 is provided below the membrane 10 and the channel 11 with a rotary valve 34 for connecting the channel 11 as desired to the outlet connection 8 and the eluate reservoir 17 connected to the valve element 28.

This device works as follows:

After the device has been placed in the apparatus belonging to it and the various inlets and outlets are connected, compressed air is supplied to the connecting channel 30, which compressed air passes by way of the non-return valve 29 into the container 1, and due to the pressure built up therein, the mixture of basic material, chaotropic substance and silica particles present therein is forced through the non-return valve 31 into the valve element 28, where the mixture is filtered and the silica particles remain behind on the membrane 10, and the fluid passes through the channel 11 and the rotary valve 34 into the outlet connection 8 and the connected outlet. The non-return valve 32 in this case remains closed, so that no fluid can pass into the connecting channel 33. Washing fluids are then introduced by way of the connecting channel 33 and the non-return valve 32 directly into the valve element 28 with the filter membrane 10, which can be washed with a relatively small volume of washing fluid. The non-return valve 31 ensures that a seal is provided relative to the container 1. After the rotary valve 34 has rotated in order to produce the connection between the channel 11 and the eluate reservoir 17, eluate is fed through the connecting channel 33 and the non-return valve 32 to the valve element 28, and the eluant fluid with nucleic acid dissolved therein passes through the membrane 10 with silica particles and by way of the channel 11 into the eluate reservoir.

The invention is not restricted to the exemplary embodiments shown in the drawing and described above, which can be varied in various ways within the scope of the invention. For example, mention is always made above of the sample fluid being discharged by means of compressed air or another compressed gas, but it is, of course, also possible to force the sample fluid out of the container 1 by mechanical means. For example, a hollow plunger could be provided in the essentially cylindrical container, in which case a small channel in the plunger is initially shut off by a seal and through the downward movement thereof in the container, the fluid in the container is pressed out through the filter. In the bottom position, the seal can then be pierced, following which the washing fluids and finally the eluant fluid can be supplied through the channel connected to the inlet in the plunger. Alternatively, it is also possible to fit a second plunger in the channel in the hollow plunger, which second plunger can be moved up and down and, after the sample fluid has been expelled, ensures that washing fluids are extracted from an inlet which is connected to the valve element by means of a non-return valve, and that said washing fluids and possibly also the eluant are then passed through the filter and the valve element. In the lowest position of the hollow plunger the plunger seals off the largest part of the container relative to the shut-off element, so that only a small volume needs to be washed, and a small quantity of washing fluid will therefore suffice.

It is also pointed out that, instead of the slidable shut-off element shown in FIGS. 1–6, a rotary shut-off element can be used. This can be comparable to the rotary valve of FIG. 7, but it is also possible to form the passage channels as recesses on the periphery of the rotary valve. In one position a first recess provides the passage to the outlet, while this first recess in a second position provides the venting, and a second peripheral recess permits the passage of eluant fluid to the eluate reservoir. The needle elements for eluate passage and venting are formed at a position below the rotary valve in this embodiment.

What is claimed is:

1. A device for use in the isolation of a biological material from a basic material containing said biological material and binding said biological material to a solid phase, comprising a container for holding a mixture of the basic material and a solid phase which binds the biological material;

a connector for connecting and disconnecting the container to an inlet for washing fluid and eluant fluid;

a connector for connecting and disconnecting the container to an outlet for the washing fluid after washing the biological material bound to the solid phase, and a connector for connecting and disconnecting the container to an eluant reservoir for collection of the eluant fluid with the dissolved biological material;

a filter which is constructed so as to allow the passage of fluid and is capable of retaining the solid phase, said filter being positioned between the container and the outlets, wherein the connector to the outlet for the washing fluid and the connector to the eluate reservoir are coupled to a shut-off element which is constructed so as to direct a fluid flow from the container either to the outlet for the washing fluid, or to the eluate reservoir; and an inlet element which can be connected to the inlet and is movable between a top position for discharging sample fluid and a bottom position for passing through washing fluid and eluant fluid.

2. The device according to claim 1, in which the shut-off element is provided with a septum and an outlet channel for allowing the passage of fluid from the filter to the outlet, and is further provided with a hollow needle element connected to the filter, for piercing the septum in order to connect the filter to the eluate reservoir.

3. The device according to claim 2, in which the needle element is fitted so that it is stationary, and the shut-off element with the septum is fitted so that it can be moved in the direction of the needle element.

4. The device according to claim 2, in which the eluate reservoir comprises a container shut off by a second septum.

5. The device according to claim 2, wherein the eluate reservoir is immovably fixed to the shut-off element provided with a septum.

6. The device according to claim 1, in which the filter is a filter membrane.

7. The device according to claim 1, in which the container is provided with two sections lying on above the other and separated by a constriction and the inlet element is movable between a position above the constriction and a position connecting in a close fit to the constriction.

8. The device according to claim 7, in which the inlet element is in the form of a hollow pin having snap elements at the end for engagement with the constriction.

9. The device according to claim 7, in which the inlet element is suspended from a flexible cover of the container, which permits the movement of the inlet element.

10. The device according to claim 1, in which the shut-off element is a valve element designed with at least one non-return valve between the inlet and the container.

11. The device according to claim 10, in which the valve element is provided with three non-return valves: a first non-return valve in a connection to a compressed gas supply, a second non-return valve between the container and the separating means, and a third non-return valve in a connection between the separating means and the inlet for the washing fluid and the eluant fluid.

12. The device according to claim 10, in which the valve element is further provided with a rotary or slide valve, for connecting the separating means to the outlet and the eluate reservoir, respectively.

13. The device according to claim 1, wherein said connector for connecting and disconnecting the container to an inlet comprises a shut off element.

14. The device of claim 1, wherein said inlet element comprises a hollow pin capable of being moved, by application of pressure, from said top position to said bottom position.

* * * * *